(12) United States Patent
Gunderson

(10) Patent No.: US 9,008,773 B2
(45) Date of Patent: Apr. 14, 2015

(54) IDENTIFICATION OF INSULATION BREACH USING ELECTROGRAMS

(71) Applicant: Medtronic, Inc., Minneapolis, MN (US)

(72) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 40 days.

(21) Appl. No.: 13/835,600

(22) Filed: Mar. 15, 2013

(65) Prior Publication Data

US 2014/0277229 A1 Sep. 18, 2014

(51) Int. Cl.
- *A61N 1/39* (2006.01)
- *A61N 1/37* (2006.01)
- *A61N 1/08* (2006.01)
- *A61N 1/362* (2006.01)

(52) U.S. Cl.
CPC ............ *A61N 1/3931* (2013.01); *A61N 1/3706* (2013.01); *A61N 1/3943* (2013.01); *A61N 1/3962* (2013.01); *A61N 1/08* (2013.01); *A61N 1/362* (2013.01); *A61N 2001/083* (2013.01)

(58) Field of Classification Search
CPC . A61N 1/365; A61N 1/36521; A61N 1/3718; A61N 1/371; A61N 1/3706; A61N 1/3702
USPC ......... 600/509; 607/8, 509, 119, 17, 120, 122
See application file for complete search history.

(56) References Cited

U.S. PATENT DOCUMENTS

| | | | |
|---|---|---|---|
| 5,344,430 A * | 9/1994 | Berg et al. ........................ 607/8 |
| 5,354,316 A | 10/1994 | Keimel | |
| 5,545,186 A | 8/1996 | Olson | |
| 5,897,577 A * | 4/1999 | Cinbis et al. .................... 607/28 |
| 6,393,316 B1 | 5/2002 | Gillberg | |
| 7,242,978 B2 | 7/2007 | Cao | |
| 7,266,409 B2 | 9/2007 | Gunderson | |
| 7,277,757 B2 | 10/2007 | Casavant | |
| 7,289,851 B2 | 10/2007 | Gunderson | |
| 7,747,320 B1 | 6/2010 | Kroll | |
| 7,783,354 B2 | 8/2010 | Gunderson | |
| 8,200,330 B2 | 6/2012 | Kroll | |

(Continued)

OTHER PUBLICATIONS

Leong, DP, et al. "Unrecognized Failure of Narrow Caliber Defibrillation Lead: The Role of Defibrillation Threshold Testing in Identifying an Unprotected Individual" PACE 2012; 1-2.

(Continued)

*Primary Examiner* — Carl H Layno
*Assistant Examiner* — Erin Piateski
(74) *Attorney, Agent, or Firm* — Michael C. Soldner

(57) ABSTRACT

An implantable medical device capable of sensing cardiac signals and delivering cardiac electrical stimulation therapies is enabled to detect a short circuit condition. In one embodiment, a cardiac signal is sensed by a sensing module coupled to electrodes. A controller identifies signal events in response to the cardiac signal and detects a short circuit condition in response to at least one of the signal events having an amplitude crossing a short circuit detection threshold and a maximum of two signal events crossing the short circuit detection threshold occurring between two adjacent events having amplitudes not crossing the short circuit detection threshold. In one embodiment, the signal events are identified from a differential signal determined from the sensed cardiac signal.

21 Claims, 6 Drawing Sheets

(56) References Cited

U.S. PATENT DOCUMENTS

| | | | |
|---|---|---|---|
| 2004/0064161 A1* | 4/2004 | Gunderson et al. | 607/28 |
| 2005/0137636 A1* | 6/2005 | Gunderson et al. | 607/27 |
| 2006/0116733 A1 | 6/2006 | Gunderson | |
| 2006/0235476 A1* | 10/2006 | Gunderson et al. | 607/5 |
| 2008/0161870 A1* | 7/2008 | Gunderson | 607/5 |
| 2008/0161872 A1* | 7/2008 | Gunderson | 607/27 |
| 2008/0215110 A1* | 9/2008 | Gunderson | 607/27 |
| 2009/0299422 A1* | 12/2009 | Ousdigian et al. | 607/5 |
| 2010/0023084 A1* | 1/2010 | Gunderson | 607/28 |
| 2010/0114222 A1* | 5/2010 | Gunderson et al. | 607/8 |
| 2010/0228307 A1* | 9/2010 | Kroll et al. | 607/7 |
| 2010/0318149 A1* | 12/2010 | Kuhn et al. | 607/18 |
| 2011/0184481 A1* | 7/2011 | Hoeppner et al. | 607/5 |
| 2011/0319957 A1* | 12/2011 | Naware et al. | 607/28 |
| 2013/0013038 A1 | 1/2013 | Miller | |

OTHER PUBLICATIONS (PCT/US2014/021010) PCT Notification of Transmittal of the International Search Report and the Written Opinion of the International Searching Authority.

* cited by examiner

IDENTIFICATION OF INSULATION BREACH USING ELECTROGRAMS

FIELD OF THE DISCLOSURE

The disclosure relates generally to medical devices configured to deliver electrical therapies. In particular the disclosure relates to devices and methods for detecting a medical electrical lead insulation breach that could lead to a short circuit condition.

BACKGROUND

Implantable cardioverter defibrillators (ICDs) typically have the capability of delivering both low voltage therapies and high voltage therapies in response to monitoring a cardiac rhythm and detecting a need for therapy. Low voltage therapies may include bradycardia pacing, cardiac resynchronization therapy (CRT), and anti-tachycardia pacing (ATP). Low voltage therapies are typically delivered using low voltage pacing electrodes, e.g. tip or ring electrodes delivering pulses of 5 Volts or less in amplitude.

High voltage therapies such as cardioversion or defibrillation shocks are delivered in response to detecting ventricular tachycardia or ventricular fibrillation. High voltage therapies are typically delivered using high voltage coil electrodes and the housing of the ICD, often referred to as the "CAN electrode" or a "housing electrode." High voltage electrodes generally have a greater surface area and deliver high energy shock pulses, typically in the range of at least 10 Joules and up to 35 Joules.

A single lead coupled to an ICD may carry multiple electrodes, which may include either or both high voltage and low voltage electrodes. Each electrode is coupled to an electrically insulated conductor extending through the elongated lead body to facilitate electrical connection of each therapy delivery electrode to the ICD.

Short circuit conditions can sometimes occur when a therapy delivery electrode or its conductor makes electrical contact with another conductor or electrode. Lead integrity testing may be performed regularly to make lead measurements, such as lead impedance measurements, to monitor for possible short circuit, open circuit or other lead conditions. A non-contact high voltage lead fault can exist, however, and may manifest only when a high-voltage therapy is delivered, causing arcing between exposed conductors. These types of faults involving high voltage conductors are frequently undetected by low voltage lead measurements. A high voltage short circuit that occurs during delivery of a defibrillation shock is likely to prevent adequate energy from being delivered to the heart, leading to a failed therapy. Since ventricular fibrillation is a life-threatening condition, prompt detection of a potential high voltage short circuit condition is needed.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
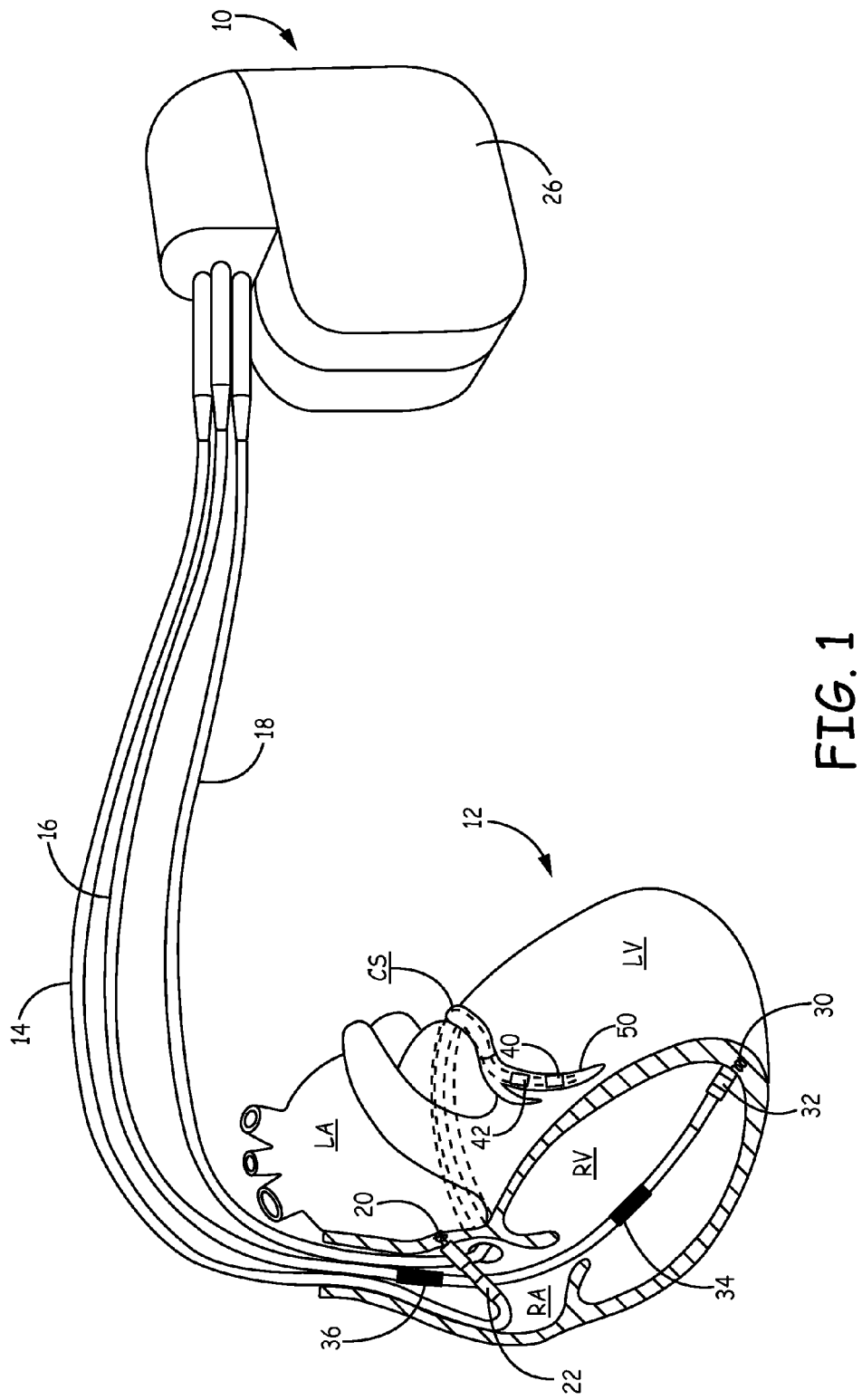
FIG. 1 is a schematic representation of an implantable medical device (IMD) capable of delivering high voltage and low voltage therapies to a heart.

FIG. 1 is a schematic representation of an implantable medical device (IMD) 10 capable of delivering high voltage and low voltage therapies to heart 12. IMD 10 is coupled to heart 12 via leads 14, 16 and 18. Right atrial lead 14 extends from IMD 10 to the right atrium (RA) and carries distal electrodes 20 and 22 for sensing cardiac electrical signals and delivering pacing pulses in the RA.

Right ventricular lead 16 carries a tip electrode 30 and a ring electrode 32 for sensing cardiac electrical signals and delivering pacing pulses in the RV. RV lead 16 additionally carries high voltage coil electrodes 34 and 36, referred to herein as the RV coil electrode 34 and the superior vena cava (SVC) coil electrode 36, for delivering high voltage cardioversion and defibrillation shocks in response to detecting a shockable tachyarrhythmia from sensed cardiac signals. In addition, a housing electrode 26, also referred to as a CAN electrode, can be formed as part of the outer surface of the housing of IMD 10 and be used as an active electrode in combination with coil electrodes 34 and/or 36 during shock delivery.

A coronary sinus (CS) lead 18 is shown extending into a cardiac vein 50 via the RA and coronary sinus for positioning electrodes 40 and 42 for sensing cardiac signals and delivering pacing pulses along the left ventricle. In some examples, CS lead 18 may additionally carry electrodes for positioning along the left atrium for sensing and stimulation along the left atrial chamber.

The depicted positions in or about the right and left heart chambers are merely illustrative. Other leads and pace/sense electrodes and/or high voltage electrodes can be used instead of, or in combination with, any one or more of the depicted leads and electrodes shown in FIG. 1. Lead and electrode configurations are not limited to transvenous leads and intravenous or intracardiac electrodes as shown in FIG. 1. In some embodiments, an IMD system may include subcutaneous electrodes, which may be carried by an extravenous lead extending from IMD 10 or leadless electrodes incorporated along the IMD housing.

IMD 10 is shown as a multi-chamber device capable of sensing and stimulation in three or all four heart chambers. It is understood that IMD 10 may be modified to operate as a single chamber device, e.g. with a lead positioned in the RV only, or a dual chamber device, e.g. with a lead positioned in the RA and a lead positioned in the RV. In general, IMD 10 may be embodied as any single, dual or multi-chamber device including lead and electrode systems for delivering at least a high voltage therapy and may be configured for delivering both high voltage shock pulses and low voltage pacing pulses.

Figure 2:
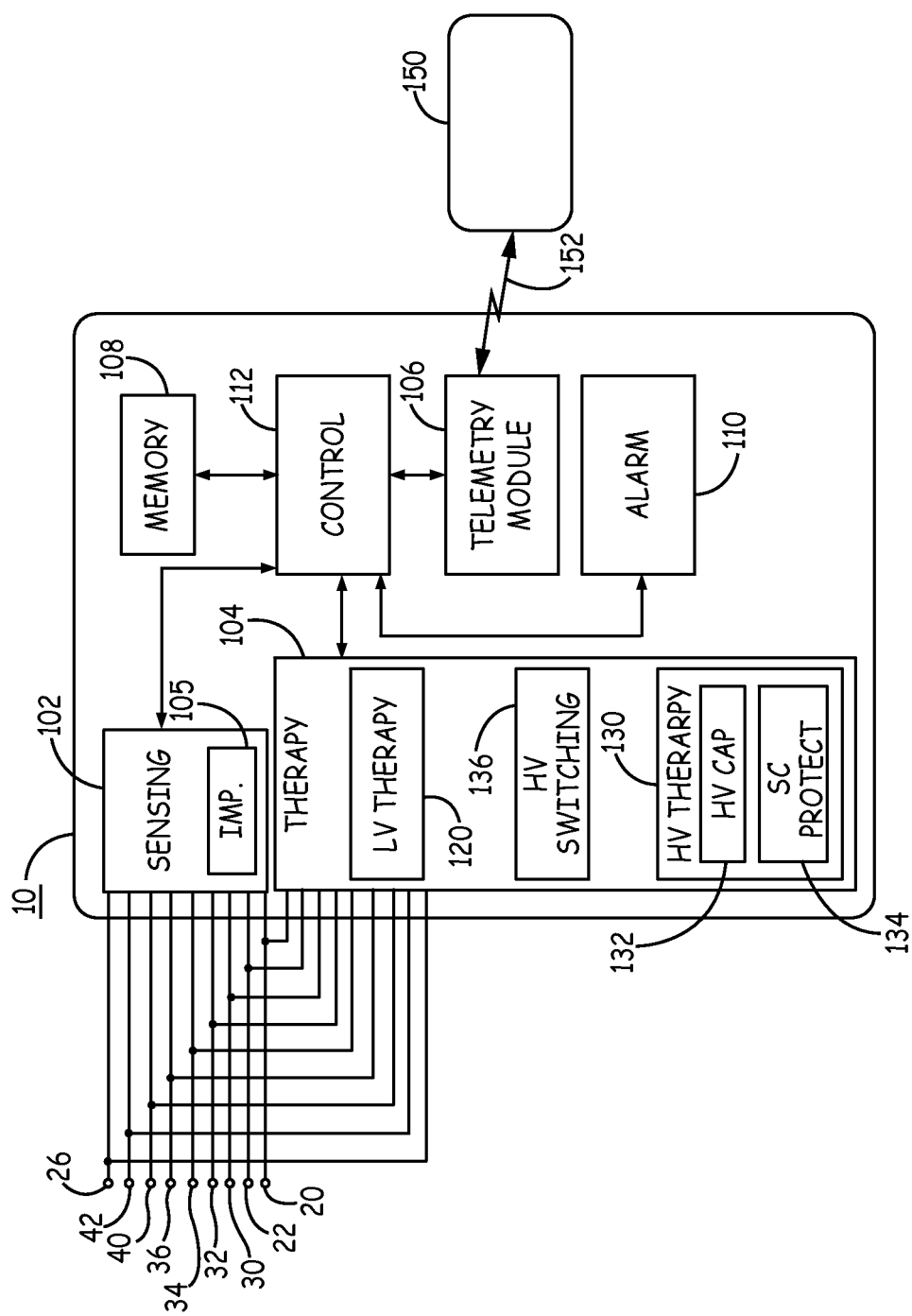
FIG. 2 is a functional block diagram of the IMD shown in FIG. 1 according to an illustrative embodiment.

FIG. 2 is a functional block diagram of the IMD 10 shown in FIG. 1 according to an illustrative embodiment. IMD 10 includes a sensing module 102, a therapy delivery module 104, a telemetry module 106, memory 108, and a control unit 112, also referred to herein as "controller" 112.

Sensing module 102 is coupled to electrodes 20, 22, 30, 32, 34, 36, 40, 42 and housing electrode 26 (all shown in FIG. 1) for sensing cardiac electrogram (EGM) signals. Sensing module 102 monitors cardiac electrical signals for sensing signals attendant to the depolarization of myocardial tissue, e.g. P-waves and R-waves, from selected ones of electrodes 20, 22, 26, 30, 32, 34, 36, 40, and 42 in order to monitor electrical activity of heart 12. Sensing module 102 may include a switch module to select which of the available electrodes are used to sense the cardiac electrical activity. The switch module may include a switch array, switch matrix, multiplexer, or any other type of switching device suitable to selectively couple electrodes to sensing module 102. In some examples, controller 112 selects the electrodes to function as sense electrodes, or the sensing vector, via the switch module within sensing module 102.

Sensing module 102 may include multiple sensing channels, each of which may be selectively coupled to respective combinations of electrodes 20, 22, 26, 30, 32, 34, 36, 40, and 42 to detect electrical activity of a particular chamber of heart 12, e.g. an atrial sensing channel and a ventricular sensing channel. Different sensing channels may additionally or alternatively be coupled to various electrode combinations for providing both near field (NF) sensing vectors and far field (FF) sensing vectors. For example, a NF sensing vector may be sensed between RV tip electrode 30 and RV ring electrode 32. A FF sensing vector may be sensed between RV coil electrode 34 and SVC coil electrode 36. Each sensing channel may comprise an amplifier that outputs an indication to controller 112 in response to sensing of a cardiac depolarization, in the respective chamber of heart 12. In this manner, controller 112 may receive sense event signals corresponding to the occurrence of R-waves and P-waves in the various chambers of heart 12. Sensing module 102 may further include digital signal processing circuitry for providing controller 112 with digitized EGM signals, which may be used to determine EGM signal features or for signal morphology analysis in some embodiments.

Sensing module 102 and control unit 112 are configured to monitor the patient's cardiac rhythm for determining a need for therapy delivery and for timing therapy delivery. In response to detecting a tachyarrhythmia, controller 112 controls therapy delivery module 104 to deliver a therapy according to programmed therapies stored in memory 108.

Sensing module 102 may include impedance monitoring circuitry 105 for measuring current between a measurement pair of electrodes 20 through 42 in response to a drive signal. The drive signal is generally a low voltage signal, and impedance measurements may be used by control 112 to detect short circuit conditions or other lead-related issues detectable when a low voltage drive signal is used. Such low voltage impedance measurements may be performed periodically or in response to loss of pacing capture or a change in pacing threshold to detect lead-related issues. As will be described herein, impedance monitoring may be controlled and adjusted to promote the identification of a short circuit condition, as evidenced by a decrease in impedance.

Sensing module 102 provides control unit 112 digitized EGM signals for detecting a possible insulation breach and short circuit condition in some embodiments. As further described below, control unit 112 includes processing circuitry for analyzing the EGM signal to detect a signature noise waveform that is characteristic of a short circuit condition. In particular, a high priority is given to monitoring for a short circuit condition that could lead to shorting of a HV shock delivered to treat a malignant tachyarrhythmia. Real-time monitoring for a short circuit condition is described herein. It is contemplated, however, that identification of a short circuit condition may be performed during post processing. An epoch of data (e.g. 10 sec) could be stored at regular intervals in the memory 108 or triggered storage based on a detected event. The data may be post-processed either within the IMD or an external device.

Therapy delivery module 104 is coupled to electrodes 20, 22, 26, 30, 32, 34, 36, 40, and 42 for delivering electrical stimulation therapy to the patient's heart. In some embodiments, therapy delivery module 104 includes low voltage (LV) therapy circuitry 120 including a pulse generator for generating and delivering LV pacing pulses during bradycardia pacing, cardiac resynchronization therapy (CRT), and anti-tachycardia pacing (ATP). Control unit 112 controls LV therapy circuitry 120 to deliver pacing pulses according to programmed control parameters using electrodes pacing electrodes 20, 22, 30, 32, 40 and/or 42 for example. Electrodes 20, 22, 30 32, 40 and 42 are generally referred to a "low voltage" electrodes because they are normally used for delivering relatively low voltage therapies such as pacing therapies as compared to the high voltage therapies, i.e. cardioversion and defibrillation therapies, delivered by high voltage coil electrodes 32 and 34. However, as will be described herein, in some instances LV electrodes 20, 22, 30, 32 40 and 42 may be used for delivering a high voltage therapy in response to detection of a high voltage short circuit condition.

Therapy delivery module 104 includes high voltage (HV) therapy delivery circuitry 130 for generating and delivering high voltage cardioversion and defibrillation shock pulses. HV therapy delivery circuitry 130 includes HV capacitors 132 that are charged in response to detecting a shockable cardiac rhythm, e.g. a ventricular tachycardia or ventricular fibrillation. After determining HV capacitors 132 have reached a targeted charge voltage, according to a programmed shock energy, HV therapy delivery 130 delivers a shock pulse via selected HV electrodes, e.g. coil electrodes 34, 36 and housing electrode 26.

HV therapy circuitry 130 includes short circuit (SC) protection circuitry for protecting IMD 10 against a short circuit fault during HV therapy delivery. In one embodiment, SC protection circuitry 134 monitors the current during the shock pulse delivery and in response to a relatively high current, i.e. very low impedance, SC protection circuitry 134 immediately terminates the shock pulse, e.g. by an electronic switch, to prevent damage to the circuitry of IMD 10. The HV short circuit condition would prevent delivery of the HV shock to the heart and would fail to terminate a detected shockable rhythm. By protecting the IMD circuitry from the SC fault, controller 112 remains operable to alter the HV therapy delivery to still treat the tachyarrhythmia and/or control therapy delivery module 104 to deliver alternative electrical stimulation therapies.

In response to identifying a short circuit condition, controller 112 may store in memory 108 an electrode vector and polarity combination being used that provided evidence of a short circuit condition. This information may be retrieved and used by a clinician in resolving the short circuit condition, e.g. by replacing a lead or reprogramming the therapy delivery electrode configuration and polarity. This information may be used by controller 112 in selecting electrode vectors and polarities for delivering future HV and/or LV therapies.

Therapy delivery module 104 includes HV switching circuitry 136 used for controlling the pathway through which HV capacitors 132 are discharged. HV switching circuitry 136 may include a switch array, switch matrix, multiplexer, or any other type of switching device suitable to selectively couple combinations of low voltage electrodes (e.g. electrodes 20, 22, 30, 32, 40 and 42) and/or high voltage electrodes (e.g. electrodes 34 and 36) and housing electrode 26 to HV therapy circuitry 130. In some examples, controller 112 selects a shock vector using any of HV coil electrodes 34, 36 and housing electrode 26. As will be described below, controller 112 may select the polarity of the electrodes included in the shock vector using switching circuitry 136.

In some embodiments, the HV capacitors may be coupled to multiple pacing electrode cathodes simultaneously, e.g. any combination or all of LV electrodes 20, 22, 30, 32, 40 and 42 for delivering a HV shock in response to a HV short circuit condition. The anode may be any of the coil electrodes 34, 36, housing electrode 26 or combination of remaining LV electrodes 20, 22, 30, 32, 40 and 42 or any other housing based or lead based electrodes that may be available in the particular IMD system. Pacing capacitors coupled to electrodes 20, 22, 30, 32, 40 and 42 included in LV therapy circuitry 120 may be used in distributing the HV charge remaining on the HV capacitor(s) 132 in some embodiments in an attempt to deliver a needed shock therapy. In this case the pacing capacitors are rated for adequately high voltage to distribute the shock energy among selected electrodes.

Controller 112 may be embodied as a processor including any one or more of a microprocessor, a digital signal processor (DSP), an application specific integrated circuit (ASIC), a field-programmable gate array (FPGA), or equivalent discrete or integrated logic circuitry. In some examples, controller 112 may include multiple components, such as any combination of one or more microprocessors, one or more controllers, one or more DSPs, one or more ASICs, or one or more FPGAs, as well as other discrete or integrated logic circuitry. The functions attributed to controller 112 herein may be embodied as software, firmware, hardware or any combination thereof. Controller 112 includes a therapy control unit that controls therapy module 104 to deliver therapies to heart 12 according to a selected one or more therapy programs, which may be stored in memory 108. Controller 112 and associated memory 108 are coupled to the various components of IMD 10 via a data/address bus.

Memory 108 stores intervals, counters, or other data used by controller 112 to control sensing module 102, therapy delivery module 104 and telemetry module 106. Such data may include intervals and counters used by controller 112 for detecting a heart rhythm and to control the delivery of therapeutic pulses to heart 12. Memory 108 also stores intervals for controlling cardiac sensing functions such as blanking intervals and refractory sensing intervals. Events (P-waves and R-waves) sensed by sensing module 102 may be identified based on their occurrence outside a blanking interval and inside or outside of a refractory sensing interval.

Memory 108 may store computer-readable instructions that, when executed by controller 112, cause IMD 10 to perform various functions attributed throughout this disclosure to IMD 10. The computer-readable instructions may be encoded within memory 108. Memory 108 may comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media, with the sole exception being a transitory propagating signal.

Tachyarrhythmia detection algorithms may be stored in memory 108 and executed by controller 112 for detecting ventricular tachycardia (VT), ventricular fibrillation (VF) as well as discriminating such ventricular tachyarrhythmias, generally referred to herein as "shockable rhythms" from atrial or supraventricular tacharrhythmias, such as sinus tachycardia and atrial fibrillation (A FIB). Ventricular event intervals (R-R intervals) sensed from the EGM signals are commonly used for detecting cardiac rhythms. Additional information obtained such as R-wave morphology, slew rate, other event intervals (e.g., P-P intervals and P-R intervals) or other sensor signal information may be used in detecting, confirming or discriminating an arrhythmia. Reference is made to U.S. Pat. No. 5,354,316 (Keimel), U.S. Pat. No. 5,545,186 (Olson et al.) and U.S. Pat. No. 6,393,316 (Gillberg et al.) for examples of arrhythmia detection and discrimination using EGM signals, all of which patents are incorporated herein by reference in their entirety. The techniques described herein for detecting a short circuit condition and responding thereto may be implemented in the types of devices disclosed in the above-referenced patents.

In response to detecting a shockable rhythm, a programmed therapy is delivered by therapy delivery module 104 under the control of controller 112. A description of high-voltage output circuitry and control of high-voltage shock pulse delivery is provided in the above-incorporated '186 Olson patent. Typically, a tiered menu of arrhythmia therapies are programmed into the device ahead of time by the physician and stored in memory 108. For example, on initial detection of a ventricular tachycardia, an anti-tachycardia pacing therapy may be selected and delivered. On redetection of the ventricular tachycardia, a more aggressive anti-tachycardia pacing therapy may be scheduled. If repeated attempts at anti-tachycardia pacing therapies fail, a HV cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold.

In the event that ventricular fibrillation is identified, high frequency burst stimulation may be employed as the initial attempted therapy. Subsequent therapies may be delivery of HV defibrillation shock pulses, typically in excess of 5 Joules, and more typically in the range of 20 to 35 Joules. Lower energy levels may be employed for cardioversion. In the absence of a HV short circuit condition, the defibrillation pulse energy may be increased in response to failure of an initial pulse or pulses to terminate fibrillation.

IMD 10 may additionally be coupled to one or more physiological sensors. Physiological sensors may include pressure sensors, accelerometers, flow sensors, blood chemistry sensors, activity sensors or other physiological sensors known for use with implantable cardiac stimulation devices. Physiological sensors may be carried by leads extending from IMD 10 or incorporated in or on the IMD housing. Sensor signals may be used in conjunction with EGM signals for detecting and/or confirming a heart rhythm.

Telemetry module 106 is used for transmitting data accumulated by IMD 10 wirelessly to an external device 150, such as a programmer, home monitor, or handheld appliance. Examples of communication techniques used by IMD 10 include low frequency or radiofrequency (RF) telemetry, which may be an RF link established via Bluetooth, WiFi, or MICS. IMD 10 may receive programming commands and algorithms from external device 150 via telemetry link 152 with telemetry module 106. For example, external device 150 may be used to program SC detection parameters used by controller 112. Telemetry module 106 may be controlled by controller 112 for delivering a patient or clinician alert or notification to external device 150 in response to detecting a short circuit condition.

IMD 10 may optionally be equipped with alarm circuitry 110 for notifying the patient or other responder that a patient alert condition has been detected by IMD 10. In one embodiment, the alarm 110 may emit an audible tone or notification to alert the patient or a responder that immediate medical attention is required. For example, when a short circuit condition is detected, particularly a short circuit involving HV coil electrodes 34 and 36, alarm 110 may be used to notify the patient, a caregiver or other responder that medical attention is required. In some embodiments, alarm 110 calls an emergency number directly via a wireless communication network.

Figure 3:
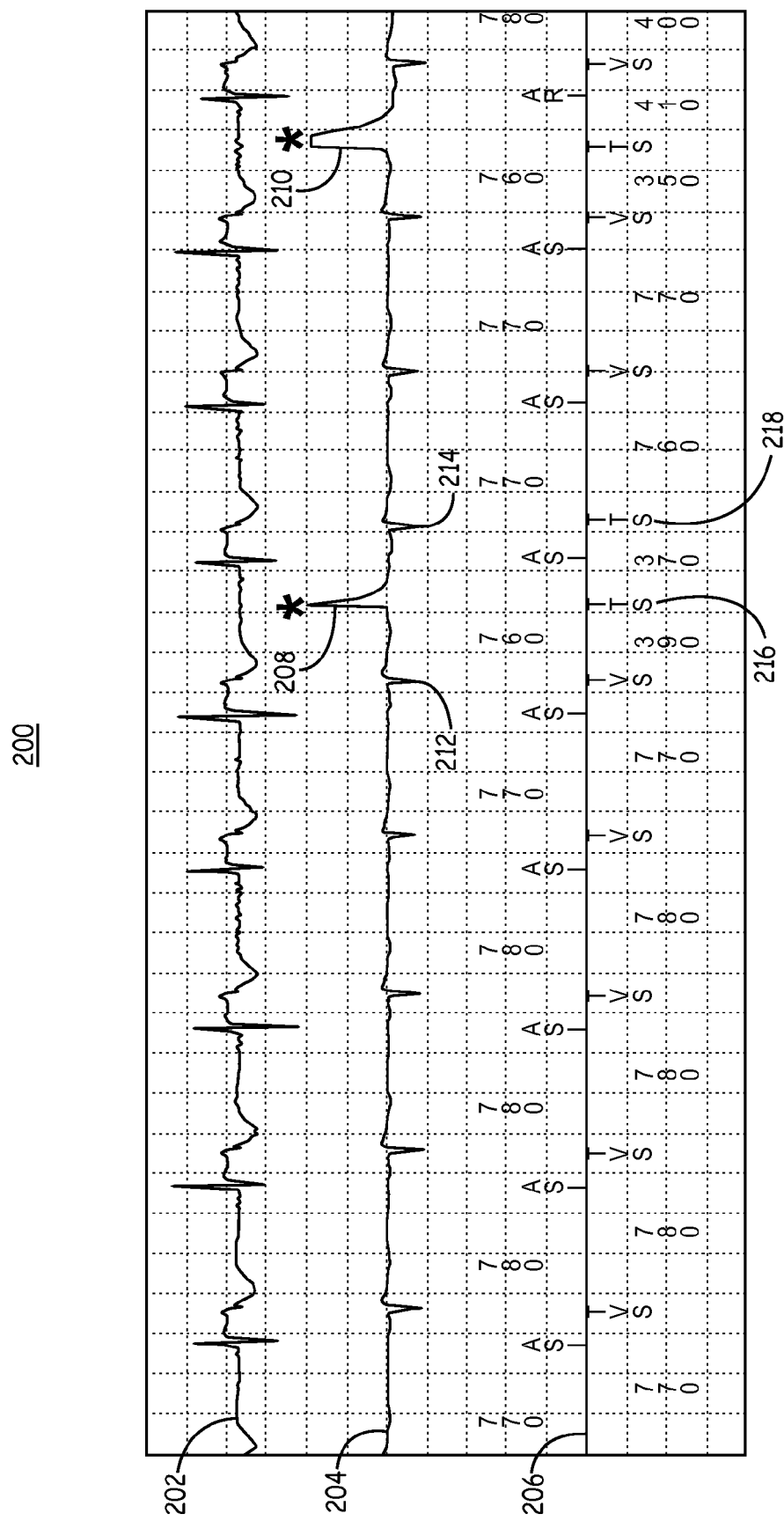
FIG. 3 shows cardiac electrogram (EGM) recordings that illustrate a signal corresponding to a short circuit condition.

FIG. 3 shows EGM recordings 200 that illustrate a signal corresponding to a short circuit condition. A NF EGM signal 202, recorded between a right atrial tip electrode and right atrial ring electrode is shown without short circuit noise signals. A FF EGM signal 204, recorded between an RV coil electrode and an SVC coil electrode, includes large noise signals 208 and 210 typifying signal events present during a potential short circuit condition associated with an insulation breach of the lead carrying the coil electrodes. These short circuit (SC) noise signals 208 and 210 are large in amplitude, singular within the true RR interval, opposite in polarity than the true R-wave signals, and occur near a central portion of the RR interval, spaced out from the adjacent, immediately preceding R-wave 212 and subsequent R-wave 214.

The SC noise signal may be the only signal peak occurring between adjacent peaks corresponding to true R-waves when a short circuit condition is present. In rarer cases, more than one, typically not more than two, short circuit signal events occur during an RR interval, e.g. during a baseline interval of the EGM signal between two true R-waves. Accordingly, a short circuit signal event can be identified as an event crossing a SC detection threshold. The SC detection threshold is set to differentiate the SC signal event from true R-waves based on amplitude and/or polarity. The timing and number of SC signal events can be used to detect a potential short circuit condition and differentiate SC signal events from other types of noise. In one embodiment, a SC condition is detected in response to at least one EGM signal event having an amplitude crossing a short circuit detection threshold and being one of a maximum of two SC signal events occurring between two adjacent events having amplitudes not crossing the SC detection threshold. The two adjacent events may correspond to normal R-waves defining an RR interval. The maximum of two short circuit signal events occurring during the RR interval, e.g. along a baseline portion of the RR interval, typifies the type of noise signal present during a short circuit condition due to a lead insulation breach.

A marker channel 206 depicts sensed events and measured event intervals. The large SC noise signals 208 and 210 are sensed as tachycardia events (TS) 216, as indicated on the marker channel, when the noise signals 208 and 210 occur within a tachycardia detection interval after the preceding R-wave. The subsequent R-wave 214 may also be sensed as a tachycardia event 218 if sensed within a tachycardia detection interval after the SC noise signal 208, which has been falsely sensed as an R-wave. As such, SC noise signals 208 and 210 may lead to R-wave oversensing and false positive ventricular tachycardia (VT) or ventricular fibrillation (VF) detection. An unnecessary therapy may result, unnecessarily using IMD battery energy. If the therapy is delivered using one or both of the RV coil electrode and SVC coil electrode associated with the SC noise signals, the therapy energy may be shorted, prematurely draining battery energy. If a therapy is delivered in response to an appropriately detected VT or VF, the short circuit condition may prevent adequate cardioversion or defibrillation therapy from being delivered to the patient.

The characteristic SC noise signal 208, 210, however, may be used to monitor for a short circuit condition. The SC noise signal 208, 210 may be distinct from other types of noise, such as low amplitude muscle noise, electromagnetic interference (EMI) noise, or noise associated with a lead conductor fracture. Other types of noise may be present in sustained or short bursts of noise signals as compared to the single noise spike of the SC noise signal 208, 210. Other types of noise may be relatively low amplitude and may be randomly located in the EGM signal relative to true sensed R-waves as compared to the relatively high amplitude SC noise signals 208, 210 occurring during a mid-portion of the RR interval. Additionally, a SC noise signal sensed on the FF EGM signal sensed between the RV coil and SVC coil electrodes is typically opposite in polarity than true R-wave signals.

Multiple EGM signals may be monitored to identify a SC condition. As shown in FIG. 3, a NF EGM signal 202, which may be an atrial signal or a ventricular signal, may be monitored simultaneously with the FF EGM signal 204. True R-waves sensed on a FF EGM signal typically have relatively lower slope and/or lower amplitude than R-waves sensed on a NF ventricular EGM signal. The high amplitude, high slope SC noise signal may therefore be more readily distinguished from true R-waves on a FF EGM signal. In some embodiments, both a FF and NF EGM signal may be sensed to enable comparisons between sensed events. Noise signals 208 and 210 are strikingly dominant on the FF EGM signal 204 and substantially absent from the NF EGM signal 202. Accordingly, a signal 208, 210 meeting other SC detection criteria and is not sensed on a NF EGM signal 202 may be detected as a SC noise signal.

Figure 4:
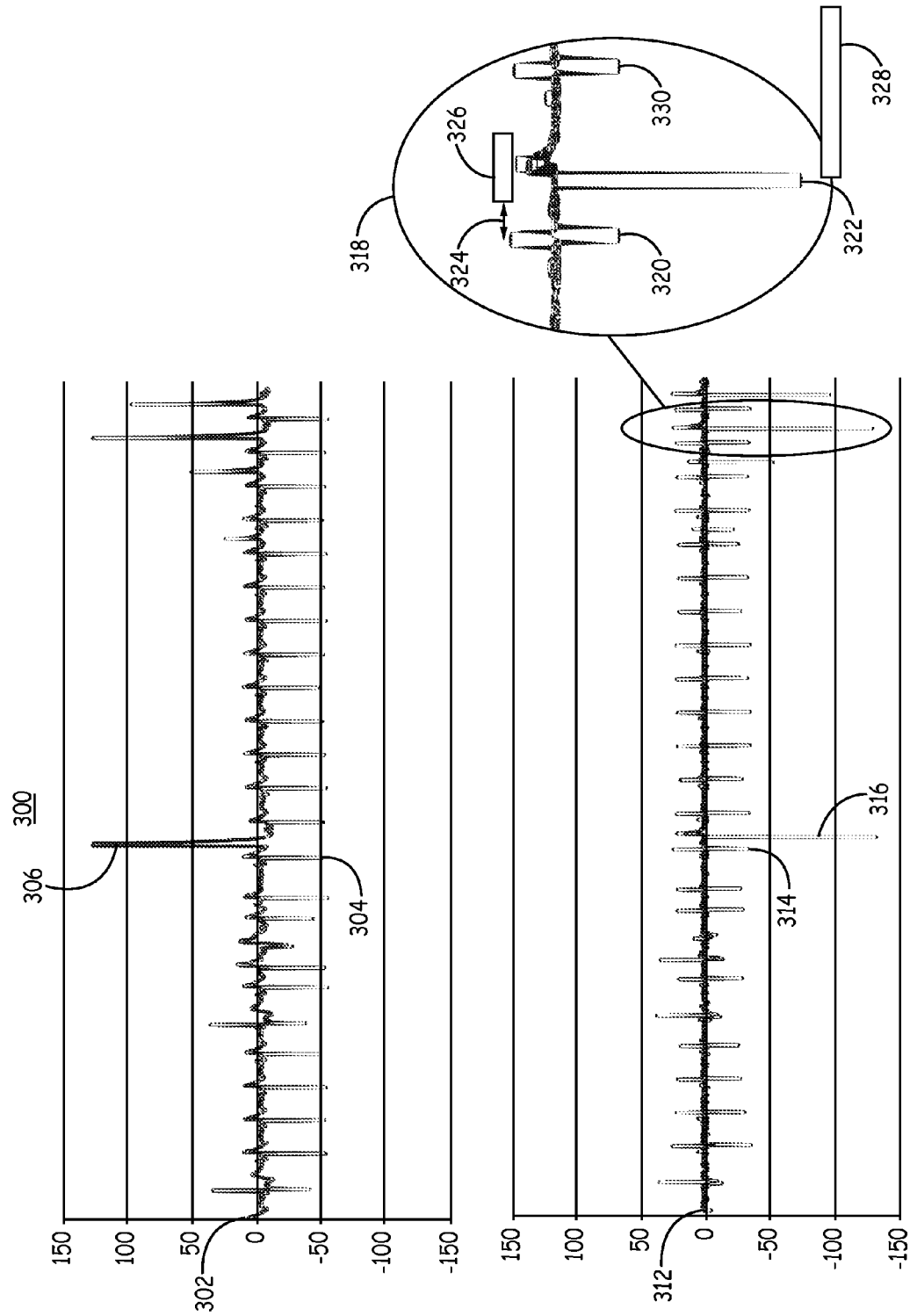
FIG. 4 shows recordings of a far-field EGM signal and a differential EGM signal 312 illustrating one technique for detecting short circuit (SC) noise signals according to some embodiments.

FIG. 4 shows recordings 300 of a FF EGM signal 302 (RV coil to SVC coil) and a differential EGM signal 312 illustrating one technique for detecting SC noise signals according to some embodiments. A large SC noise signal 306 is observed during an RR interval, following an R-wave 304 that is relatively much smaller in amplitude (absolute value). The R-waves in EGM signal 302 are generally of consistent amplitude and polarity.

A differential EGM signal 312 is computed from the raw EGM signal 302. The SC noise signal 316 is still clearly observed and the difference in the amplitude of the SC noise signal 316 and the R-wave signal 314 is even more pronounced than in the raw EGM signal 302. The differential EGM signal 312 is a first order differential signal wherein the amplitude of each differential signal sample point is determined by computing the successive amplitude differences between raw EGM signal sample points, e.g. {n−(n−1)}. While a first order differential signal is shown here, it is contemplated that higher order differential signals could be used for differentiating and identifying SC noise signals from adjacent true R-wave signals.

In some embodiments, the amplitude of the raw EGM signal and/or the differential EGM signal 312 may be compared on a sample-by-sample basis to a SC detection threshold for detecting SC signals 306 and/or 316. In other embodiments, the peak amplitude following the timing of an R-wave sense signal may be compared to the SC detection threshold. Both the true R-waves and the SC signal 306 will be detected as R-waves. As such, the timing of an R-wave sense signal received from a sense amplifier in sensing module 102 may be used to start searching for a subsequent signal peak. If the peak amplitude of the sensed signal is greater than the SC detection threshold, the signal is detected as a SC event.

The SC detection threshold may be set in a variety of ways. Since the difference between a SC noise signal 306, 316 and a true R-wave is expected to be large, a nominal threshold, e.g. in the range of 50 to 100 A/D units in the example shown, may be set as a SC detection threshold. In other embodiments, a patient-specific threshold may be set based on sensed R-wave amplitudes. A peak amplitude may be compared to a preceding peak amplitude, e.g. the peak of SC noise signal 316 of the differential signal 312 may be compared to the peak amplitude of the immediately preceding peak 314 of the differential signal 312 to identify signal 316 as a SC noise signal. If the difference between successive peak amplitude values (which may be absolute values) is greater than a predetermined threshold, the larger peak is detected as a SC noise signal.

Alternatively, a measure of multiple preceding R-wave amplitudes, e.g. a running average or other distribution measurement of preceding R-waves, may be determined and used to set a SC detection threshold. For example, a SC detection threshold may be set as some percentage greater than one or more preceding R-wave amplitudes. In one illustrative example, the SC detection threshold is 20% greater than a running average of 12 R-wave peak amplitudes. In another embodiment a non-parametric method for setting a SC detection threshold may include determining a desired number of consecutive R-wave peak amplitudes and using the nth highest peak amplitude value. For example, the most recent 12 R-wave peak amplitudes may be determined and the $3^{rd}$ highest peak amplitude value may be used to set a SC detection threshold. When comparing peak amplitudes, absolute values may be used.

If the raw EGM signal 302 is being used to identify SC noise signals, a SC detection threshold may be set as some threshold opposite in polarity than a typical R-wave peak or a typical QRS signal amplitude range. For example, using the raw EGM signal, the minimum and maximum amplitude values over a specified time range (e.g. approximately 10 seconds) may be determined during normal sensing conditions (i.e. no noise signals). If the range is, for example, between a minimum of −50 A/D units and a maximum of 10 A/D units, a SC detection threshold could be defined as any signal crossing a positive polarity threshold, e.g. +25 A/D units. In other words, a SC detection threshold may be established that allows detection of an abrupt polarity change outside a "normal" amplitude and polarity range of the raw EGM signal.

In addition to an amplitude- and/or polarity-based SC detection threshold, a timing-based SC detection threshold may be established. A SC detection window may be set at a predetermined interval after a sensed R-wave. For example, as shown in the enlarged view 318 of a portion of differential signal 312, a SC detection window 326 may be set to begin a predetermined interval 324 after a sensed R-wave 320. For example, SC detection window 326 may begin at approximately 100 to 300 ms following an R-wave sense signal 320 and may be approximately 100 to 300 ms in duration. If a single signal 322, or a maximum of two signals, exceeding the SC detection amplitude threshold (using either the raw and/or differential signal) is sensed or identified during the SC detection window 324, the signal 322 may be detected as a SC signal. The SC detection window may be set following signal events that do not cross the SC detection threshold, i.e. signal events corresponding to true R-waves.

An additional criterion may be applied that requires that only a single sensed event occurs during a subsequent monitoring window. For example, a normally sensed R-wave 330 or no signal at all may be sensed within a predetermined next time window 328 following the suspected SC noise signal 322. The next time window 328 may be set approximately equal to an expected RR interval, a window that is at least half of an RR interval since SC noise signal 322 is expected to occur in a mid-portion of the RR interval, or may be equal to SC noise detection window 326 started in response to the false sensing of the SC noise signal 322 as an R-wave. Such timing-based criteria for detecting a SC signal associated with an insulation breach may be used to positively identify the characteristic high amplitude, single noise spike that may typically occur in a mid-portion of the true RR interval, or in some cases a maximum of two SC signal events between two adjacent true R-waves.

Figure 5:
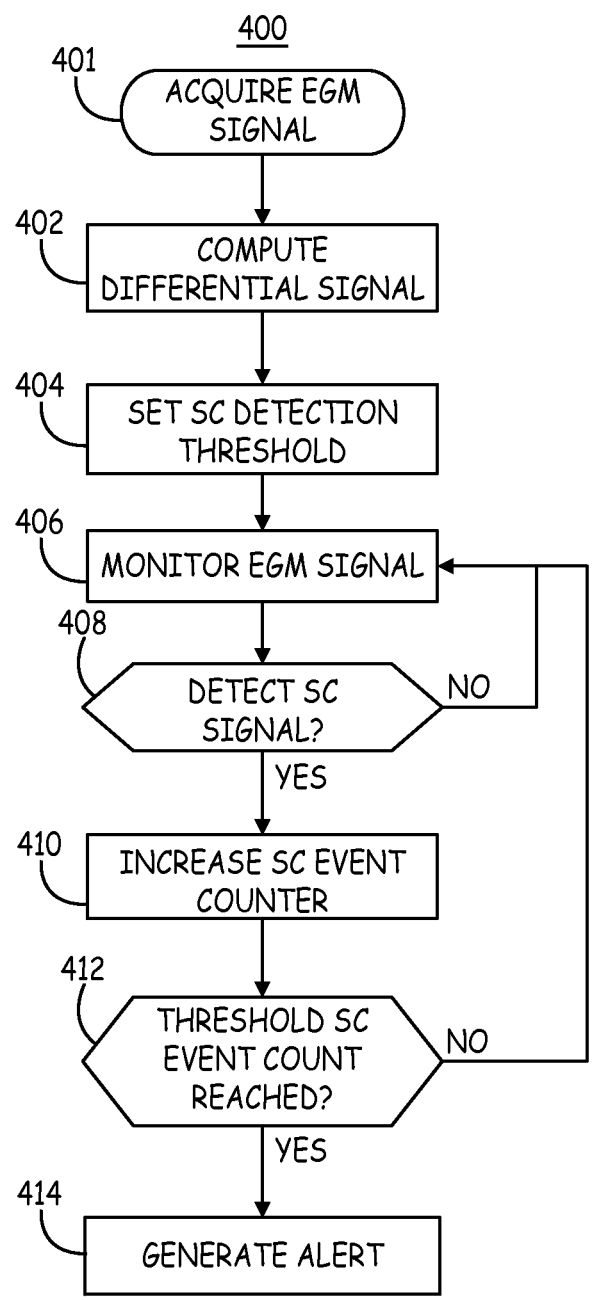
FIG. 5 is a flow chart of a method for monitoring for a short circuit condition according to one embodiment.

FIG. 5 is a flow chart 400 of a method for monitoring for a short circuit condition according to one embodiment. Flow chart 200 is intended to illustrate the functional operation of the IMD 10, and should not be construed as reflective of a specific form of software or hardware necessary to practice the methods described. It is believed that the particular form of software will be determined primarily by the particular system architecture employed in the IMD and by the particular detection and therapy delivery methodologies employed by the device. Providing software, hardware and/or firmware to accomplish the described functionality in the context of any modern IMD, given the disclosure herein, is within the abilities of one of skill in the art. Methods described in conjunction with flow charts presented herein may be implemented, at least in part, in a non-transitory computer-readable medium that stores instructions for causing a programmable processor to carry out the methods described. The instructions may be implemented as one or more software modules, which may be executed by themselves or in combination with other software by controller 112 in cooperation with therapy delivery module 104 and sensing module 102.

At block 401, an EGM signal is sensed. In one embodiment, the EGM signal is a FF EGM. The FF EGM signal being monitored for a SC condition will typically include at least one HV coil electrode and may be between two HV coil electrodes, such as RV coil 34 and SVC coil 36 shown in FIG. 1. With reference to IMD 10 shown in FIG. 2, sensing module 102 provides a digitized FF EGM signal to controller 112 for monitoring for SC signals.

At block 402, the controller 112 computes a differential signal of the raw digitized EGM signal. It is contemplated that in some embodiments, SC detection criteria may be applied to the raw digitized EGM signal additionally or alternatively to the differential EGM signal. As described above, however, the differential signal is expected to provide a greater difference between true R-wave signal amplitude and slope and SC noise signal amplitude and slope, which may increase the reliability of SC noise signal detection.

A SC detection threshold is established at block 404. The SC detection threshold may include any combination of an amplitude-based threshold (including polarity change detection) and the timing-based thresholds as described above. For example, a nominal amplitude threshold and SC detection window may be applied by controller 112 for detecting SC noise signals. Alternatively, a patient-specific amplitude threshold may be computed by controller 112 using previously sensed R-waves. A patient-specific SC detection window may be computed based on previously measured RR intervals. Patient-specific amplitude thresholds and SC detection windows may be updated over time using running averages, an nth largest value out of m values, or other updated measurements of R-wave amplitude and RR intervals.

At block 406, the controller 112 monitors the FF EGM signal events for SC noise signals by applying the SC detection threshold criteria to the differential signal. If a SC noise signal is detected at decision block 408, a SC event counter may be increased at block 410. The raw and/or differential EGM signals that resulted in increasing the SC event counter may be stored in IMD memory 108, for example along with marker channel data, for later retrieval and review by a clinician or other expert for confirmation of a short circuit condition. If the SC event counter reaches a threshold event count, as determined at block 412, an alert signal is generated at block 414. A patient alert may be generated by the IMD 10 and/or a telemetry alert signal may be transmitted to an external device 150 via wireless telemetry to notify the patient or a clinician of the detected SC condition. In some embodiments, a single detected SC noise signal may trigger an alert at block 414. In other embodiments, a threshold number of three or more SC events may be required before triggering an alert.

Figure 6:
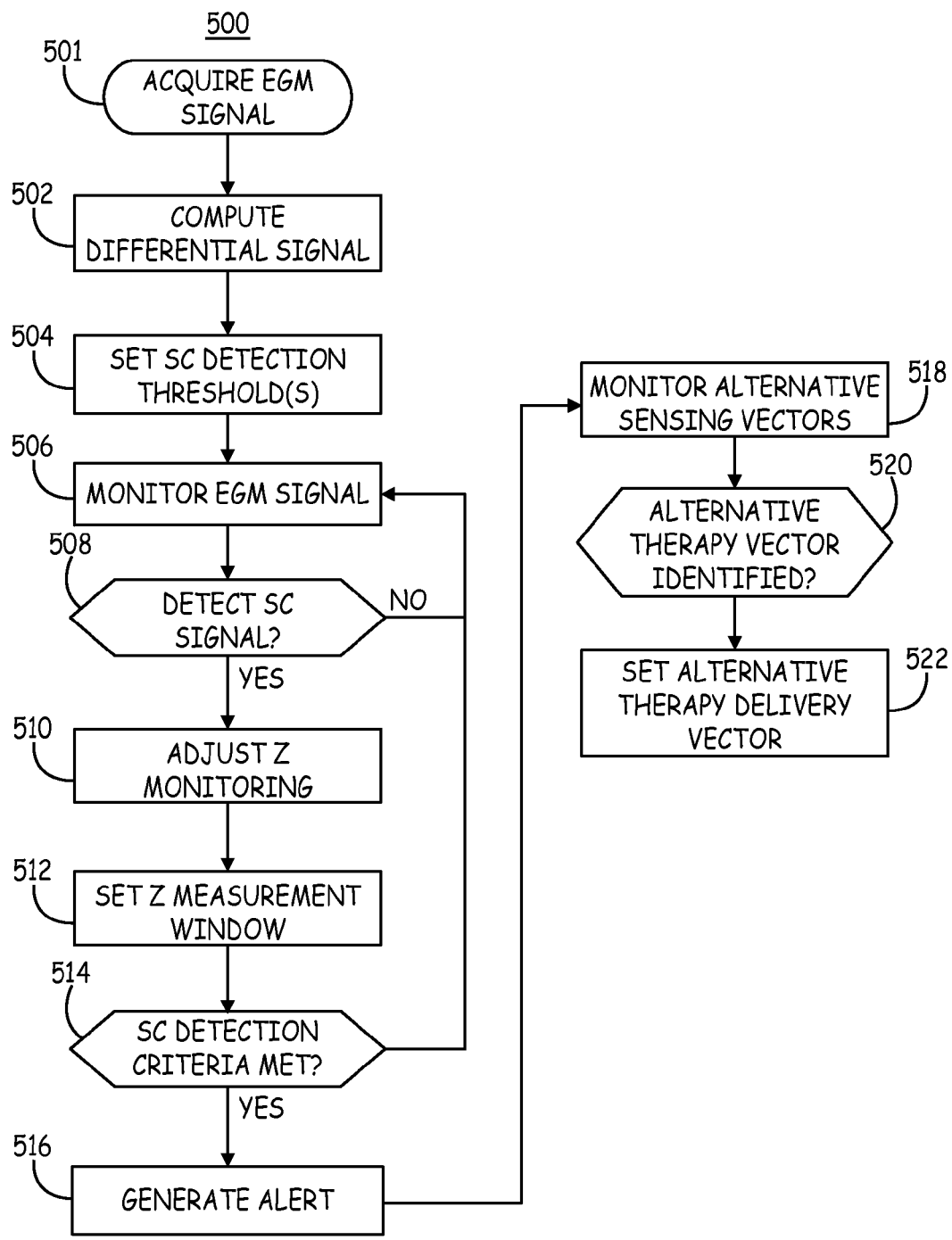
FIG. 6 is a flow chart of a method for detecting and responding to a SC condition according to an alternative embodiment.

FIG. 6 is a flow chart 500 of a method for detecting and responding to a SC condition according to an alternative embodiment. At block 501, an EGM signal, typically a FF EGM signal including RV coil electrode 34 and SVC coil electrode 36 is acquired. At block 502, a differential signal of the raw EGM signal is computed by controller 112. The controller 112 establishes SC detection thresholds at block 504, e.g. according to programmed nominal values and/or measured R-wave amplitude, R-wave polarity, RR intervals or any combination thereof, for detecting SC noise signals. The controller 112 monitors the EGM signal for SC noise by applying the SC detection threshold criteria to the differential signal at block 506 as described previously herein.

If at least one SC signal event is detected at block 508, controller 112 adjusts the impedance (Z) monitoring performed by sensing module 102 to increase the likelihood of measuring an impedance change associated with the short circuit condition. Impedance monitoring may typically be performed once per day or perhaps every six hours or some other periodic interval. In response to detecting one or more SC signals at block 508, controller 112 adjusts impedance monitoring performed by sensing module 102 to include frequent impedance measurements of the FF EGM sensing vector pathway, or whichever EGM sensing pathway was used to detect the SC signal event(s). For example, the impedance may be measured hourly, every 30 minutes, every 15 minutes, or some other periodic interval that is relatively more frequent than the previous impedance monitoring schedule being used by sensing module 102. The increased frequency of impedance monitoring may be performed at frequent intervals, e.g. every 30 minutes, for some interval of time, e.g. 12 or 24 hours, after detecting a SC noise signal.

In addition to adjusting a frequency of impedance monitoring, an impedance monitoring window may be set at block 512 in an attempt to measure the impedance of the sensing pathway during or near the expected time of a SC noise signal, i.e. approximately a mid-portion or baseline portion of the RR interval. Accordingly, an impedance measurement window may be set at block 512 that corresponds approximately to a SC detection window as described above in conjunction with FIG. 4. The impedance may be measured continuously during the impedance measurement window or repeatedly during the impedance measurement window, e.g. two or more times during the measurement window. It is recognized that impedance monitoring may occur both within and outside an impedance measurement window set to specifically identify a change in impedance that may occur during a mid-portion or baseline portion of the RR interval associated with a SC signal.

At block 514, the controller 112 determines if the SC detection criteria are met. SC detection criteria may include a predetermined number of SC signal events being detected and may include detection of a change in impedance of the sensing pathway. A change in impedance may be a decrease in impedance, occurring within or outside an impedance measurement window, as compared to one or more previous impedance measurements.

In response to detecting a SC condition, an alert is generated at block 516. In addition to generating an alert, alternative sensing vectors may be monitored at block 518 for detecting the SC condition. One or more alternative EGM sensing vectors may be monitored by controller 112 to detect SC noise signals. For example, if SC noise signals are detected on the FF EGM signal sensed between the RV coil and SVC coil electrodes, an EGM signal sensed between the RV coil and the RV tip or RV ring electrode and an EGM signal sensed between the SVC soil and the RV tip or RV ring electrode may both be monitored to determine if a different sensing pathway does not result in SC noise signal detection. Other available LV sense/pace electrodes may be paired with the RV coil and with the SVC coil until a pathway is identified that does not result in SC noise signal detection. It is recognized that for different sensing pathways, different SC detection thresholds may be used.

If an alternative sensing pathway can be identified at block 520 that does not include SC noise signals, a therapy delivery vector may be set by the controller 112 at block 522 using this information. For example, if an SVC coil to RV tip sensing pathway results in no SC noise signal detection but the RV coil to RV tip sensing pathway does result in SC noise signal detection, a HV therapy delivery vector may be selected to include the SVC coil and exclude the RV coil for delivering HV cardioversion or defibrillation shocks. In this way, controller 112 can use SC condition detection results to identify a therapy delivery pathway and control therapy delivery module 104 to deliver therapy, at least a high voltage therapy, as needed using a pathway that may exclude the short circuit condition.

Thus, a medical device and associated methods for detecting and responding to a short circuit condition have been presented in the foregoing description with reference to specific embodiments. Various combinations or modifications of the illustrative embodiments may be conceived by one having ordinary skill in the art based on the teachings provided herein. It is appreciated that various modifications to the referenced embodiments may be made without departing from the scope of the disclosure as set forth in the following claims.

The invention claimed is:

1. An implantable medical device, comprising:
a plurality of electrodes carried by at least one lead;
a sensing module coupled to the plurality of electrodes for sensing a cardiac signal;
a controller coupled to the sensing module and configured to:
determine a plurality of signal events in response to the cardiac signal; and
detect a short circuit condition in response to at least one of the plurality of signal events having an amplitude crossing a short circuit detection threshold and a maximum of two signal events crossing the short circuit detection threshold occurring during a time interval between two adjacent signal events defining the time interval and having amplitudes not crossing the short circuit detection threshold.

2. The device of claim 1, wherein controller is further configured to:
identify the two adjacent signal events as normal R-waves defining an R-R interval; and
detect the short circuit condition in response to the maximum of two of the plurality of signal events having an amplitude greater than the short circuit detection threshold occurring during a mid-portion of the R-R interval.

3. The device of claim 1, wherein the controller is further configured to determine a differential signal in response to the sensed cardiac signal, the plurality of signal events being identified from the differential signal.

4. The device of claim 1, wherein the controller is further configured to determine the short circuit detection threshold in response to at least one of a previously determined R-wave amplitude and a previously determined R-wave polarity.

5. The device of claim 1, wherein the sensing module is configured to determine cardiac sense event signals in response to the cardiac signal;
the controller being further configured to:
set a short circuit detection window having an onset spaced in time after a sense event signal received from the sensing module; and
detect the short circuit condition in response to the at least one of the plurality of signal events having an amplitude greater than the short circuit detection threshold during the short circuit detection window.

6. The device of claim 5, wherein the controller is further configured to:
set a next window in response to the at least one of the plurality of signal events having an amplitude greater than the short circuit detection threshold during the short circuit detection window; and
detect the short circuit condition in response to not more than one of the plurality of signal events being during the next window.

7. The device of claim 1, further comprising an impedance measuring circuit;
the controller configured to control the impedance measuring circuit to increase a frequency of impedance measurements in response to detecting the at least one of the plurality of signal events having an amplitude greater than the short circuit detection threshold.

8. The device of claim 1, further comprising an impedance measuring circuit;
the controller configured to control the impedance measuring circuit to determine an impedance during a time window set an interval after one of the plurality of signal events not exceeding the short circuit detection threshold.

9. The device of claim 1, wherein the controller further configured to generate an alert signal in response to detecting the short circuit condition.

10. The device of claim 1, further comprising a therapy delivery module;
the controller further configured to identify a therapy delivery pathway in response to detecting the short circuit condition and control the therapy delivery module to deliver a therapy using the identified pathway.

11. A method, comprising:
sensing a cardiac signal by a sensing module coupled to a plurality of electrodes;
determining a plurality of signal events in response to the cardiac signal;
and detect a short circuit condition in response to at least one of the plurality of signal events having an amplitude crossing a short circuit detection threshold and a maximum of two signal events crossing the short circuit detection threshold occurring during a time interval between two adjacent signal events defining the time interval and having amplitudes not crossing the short circuit detection threshold.

12. The method of claim 11, further comprising:
identifying the two adjacent signal events as normal R-waves defining an R-R interval; and
detecting the short circuit condition in response to at least one of the plurality of signal peaks having an amplitude greater than the short circuit detection threshold and occurring during a mid-portion of the R-R interval.

13. The method of claim 11, further comprising determining a differential signal in response to the sensed cardiac signal, the plurality of signal events being identified from the differential signal.

14. The method of claim 11, further comprising determining the short circuit detection threshold in response to at least one of a previously determined R-wave amplitude and a previously determined R-wave polarity.

15. The method of claim 11, further comprising:
determining cardiac sense event signals in response to the cardiac signal;
setting a short circuit detection window having an onset spaced in time after a sense event signal received from the sensing module;
detecting the short circuit condition in response to the at least one of the plurality of signal events having an amplitude greater than the short circuit detection threshold during the short circuit detection window.

16. The method of claim 15, further comprising:
setting a next window in response to the at least one of the plurality of signal events having an amplitude greater than the short circuit detection threshold during the short circuit detection window; and
detecting the short circuit condition in response to not more than one of the plurality of signal events being during the next window.

17. The method of claim 11, further comprising increasing a frequency of impedance measurements in response to detecting the at least one of the plurality of signal events having an amplitude greater than the short circuit detection threshold.

18. The method of claim 11, further comprising controlling an impedance measuring circuit to determine an impedance during a time window set an interval after one of the plurality of signal events not exceeding the short circuit detection threshold.

19. The method of claim 11, further comprising generating an alert signal in response to detecting the short circuit condition.

20. The method of claim 11, further comprising identifying a therapy delivery pathway in response to detecting the short circuit condition and controlling a therapy delivery module to deliver a therapy using the identified pathway.

21. A non-transitory, computer-readable medium storing a set of instructions which cause a controller of an implantable medical device to:
sense a cardiac signal by a sensing module coupled to a plurality of electrodes;
determine a plurality of signal events in response to the cardiac signal; and
detect a short circuit condition in response to at least one of the plurality of signal events having an amplitude crossing a short circuit detection threshold and a maximum of two signal events crossing the short circuit detection threshold occurring during a time interval between two adjacent signal events defining the time interval and having amplitudes not crossing the short circuit detection threshold.

\* \* \* \* \*